United States Patent [19]

Bigg et al.

[11] Patent Number: 4,904,684
[45] Date of Patent: Feb. 27, 1990

[54] 2-(4,5-DIHYDRO-1H-IMIDAZOL-2-YL)-1,2,4,5-TETRAHYDROPYRROLO[3,2,1-HI]INDOLE DERIVATIVES USEFUL AS ANTIDIABETIC AGENTS

[75] Inventors: Dennis Bigg, Castres; Salomon Langer, Paris; Claude Morel, Cresly-Magny-les-Hameaux; Mireille Sevrin, Paris, all of France

[73] Assignee: Synthelabo, Paris, France

[21] Appl. No.: 236,423

[22] Filed: Aug. 25, 1988

[30] Foreign Application Priority Data

Oct. 7, 1987 [FR] France .................................. 87 13831

[51] Int. Cl.$^4$ ............................................. A61K 31/415
[52] U.S. Cl. ...................................... 514/402; 514/866
[58] Field of Search .................................. 514/402, 866

[56] References Cited

U.S. PATENT DOCUMENTS

| | | | |
|---|---|---|---|
| 3,671,541 | 6/1972 | Bormann et al. | 260/309.6 |
| 4,391,814 | 7/1983 | Vorbruggen | 424/273 R |
| 4,411,908 | 10/1983 | Chapleo et al. | 424/273 R |
| 4,617,313 | 10/1986 | Bigg et al. | 514/402 |

*Primary Examiner*—Frederick E. Waddell
*Attorney, Agent, or Firm*—Wegner & Bretschneider

[57] ABSTRACT 2-(4,5-Dihydro-1H-imidazol-2-yl)-1,2,4,5-tetrahydropyrrolo[3,2,1-hi]indole derivatives and their pharmaceutically acceptable salts are useful an antidiabetic agents.

5 Claims, No Drawings

2-(4,5-DIHYDRO-1H-IMIDAZOL-2-YL)-1,2,4,5-TETRAHYDROPYRROLO[3,2,1-HI]INDOLE DERIVATIVES USEFUL AS ANTIDIABETIC AGENTS

The present invention relates to antidiabetic compositions containing 2-(4,5-dihydro-1H-imidazol-2-yl)-pyrrolo[3,2,1-hi]indole derivatives, and their use in a method of treatment of diabetes.

Said derivatives are disclosed in U.S. Pat. No. 4,617,313; their general formula the following

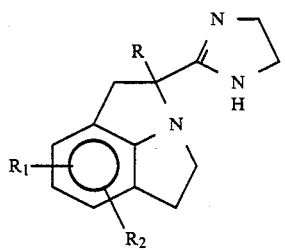

in which R is hydrogen or a linear or branched $C_{1-4}$ alkyl group, and $R_1$ and $R_2$, which may be the same or different, are hydrogen, halogen or $C_{1-4}$ alkyl.

They can exist in the forms of pure enantiomers or mixture thereof, and also in the form of free bases or addition salts with pharmaceutically acceptable acids.

They can be prepared according to the method described in the abovementioned patent. The enantiomers can be prepared from the racemates by fractional crystallization of the addition salts they form with the enantiomers of optically active acids, such as tartaric acid or dibenzoyltartaric acid.

The following examples illustrate the invention.

EXAMPLE 1

2-(4,5-Dihydro-1H-imidazol-2-yl)-1,2,4,5-tetrahydropyrrolo[3,2,1-hi]indole (a) Ethyl 1,2,4,5-tetrahydro-pyrrolo[3,2,1-hi]indole-2-carboxylate.

In a 1,000-ml three-necked flask equipped with a magnetic stirrer, hydrogen chloride gas inlet, air-cooled condenser with calcium chloride guard tube and thermometer, placed in a bath of dry ice and isopropyl alcohol, 15.8 g (0.073 mol) of ethyl 4,5-dihydro-pyrrolo[3,2,1-hi]indole-2-carboxylate are introduced with 150 ml of ethanol. The mixture is cooled to −20° C. and hydrogen chloride gas is condensed in at this temperature until a solution is obtained. 26.1 g (0.22 gram-atom) of granulated tin are then added in a single portion, the cold bath is removed and stirring is maintained for 20 hours at room temperature. A yellow suspension is obtained, and this is concentrated on the water bath and taken up in 550 ml of absolute ethanol. The mixture is cooled, ammonia is bubbled in until the pH equals 9 to 10 to precipitate the tin salts, the latter are drained while being washed with iced ethanol and the filtrate obtained is evaporated to dryness. The residue is subjected to chromatography on a silica column, eluting with dichloromethane. 11.65 g of an oily yellow product are finally collected.

(b) Ethyl 2-propyl-1,2,4,5-tetrahydro-pyrrolo[3,2,1-hi]indole-2-carboxylate.

In a 150 ml Keller flask equipped with a magnetic stirrer, thermometer, argon inlet, dropping funnel, and placed on a cold bath, there are introduced, under argon, 34 ml (2.43 g or 0.024 mol) of diisopropylamine and 20 ml of tetrahydrofuran.

The reaction mixture is cooled to −75° C., and there are then introduced 15 ml (0.024 mol) of a 1,6 M solution of butyllithium in hexane, in the course of 15 mn. The colourless, clear solution is stirred at −70° C. for 1 hour and a solution of 4.3 g (0.02 mol) of ethyl 1,2,4,5-tetrahydro-pyrrole[3,2,1-hi]indole-2- carboxylate in 15 ml of tetrahydrofuran is added at −70° C. in the course of 15 mn. The yellow-orange solution is still stirred at −70° C. for 1 hour and, in the course of 15 mn, at −70° C., a solution of 9.8 ml (17 g or 0.1 mol) of n-propyl iodide in 10 ml of tetrahydrofuran is added. The reddish suspension is still stirred at −70° C. for 1 hour, and then left at room temperature for 3 hours. Then the reaction mixture is poured into 400 ml of iced water, it is extracted with diethyl ether in the presence of a sodium chloride solution. The extract is washed with water and dried over sodium sulphate, the organic phase is separated and evaporated to dryness under vacuum on the water bath.

5.4 g of a brown liquid are obtained.

It is purified by chromatography trough a silica column with a 99/1 mixture of dichloromethane/methanol as eluent. 2.3 g of product are obtained, which is used, as it is, in the following stage.

(c) 2-(4,5-Dihydro-1H-imidazol-2-yl)-2-propyl-1,2,4,5-tetrahydro-pyrrolo[3,2,1-hi]indole.

In a 50 ml Keller flask equipped with a magnetic stirrer, reflux condenser, thermometer, argon inlet, dropping funnel and Dean-Stark apparatus, there are introduced, under argon, 6 ml of toluene and 2.9 ml (0.5 g or 0.0064 mol) of trimethylaluminium (at 25.2% strength in hexane). The mixture is cooled to −10° C. and then there is added, in the course of 10 mn, a solution of 0.45 ml (0.4 g or 0.0063 mol) of ethylenediamine in 3 ml of toluene. The mixture is still stirred for 10 mn at −10° C., it is left to return at room temperature, and then heated to 50° C., and at this temperature therr is added, in the course of 10 mn, a solution of 1.1 g (0.0042 mol) of ethyl 2-propyl-1,2,4,5-tetrahydro-pyrrolo[3,2,1-hi]indole-2-carboxylate in 6 ml of toluene.

The mixture is refluxed for 9 hours, and then left standing under argon at room temperature for a night.

After the whole mixture has been cooled to −15° C. it is hydrolyzed with 2.9 ml of water, while being stirred, and then it is extracted with ethyl acetate. The organic fractions are combined, washed with a sodium chloride solution, dried, filtered and evaporated.

1 g of a pale maroon residue is obtained, which is used, as it is, for the preparation of the hydrochloride.

(d) 2-(4,5-Dihydro-1H-imidazol-2-yl)-2-propyl-1,2,4,5-tetrahydro-pyrrolo[3,2,1-hi]indole hydrochloride.

In a 1,000-ml flask equipped with a magnetic stirrer and placed under argon, there are introduced 5.1 g (0.02 mol) of 2-(4,5-dihydro-1H-imidazol-2-yl)-2-propyl-1,2,4,5-tetrahydropyrrolo[3,2,1-hi]indole, 200 ml of diethyl ether and 100 ml of 0.1N hydrochloric dithyl ether. The salt is formed instantaneously, and it is filtered quickly.

It is taken up in diethyl ether and evaporated under vacuum. The salt is then suspended in acetone and stirred at 20° C. for 30 mn. It is filtered, dried under vacuum and recrystallized in isopropyl alcohol.

Melting point: 255° C. (decomposition).

(e) Dextro-rotatory enantiomer.

25 g (0.1 mol) of (±)-2-(4,5-dihydro-1H-imidazol-2-yl)-2-propyl-1,2,4,5-tetrahydro-pyrrolo[3,2,1-hi]indole in solution in 200 ml of methanol are treated with a solution of 15.05 g (0.1 mole) of (+)-tartaric acid in 200 ml of methanol. The solution is stirred at 20° C. for 15 mn, the solvent is evaporated under vacuum and the residue is recrystallized three times in methanol. 8.2 g of salt are obtained.

Melting point: 225°–228° C. $[\alpha]_D^{20} = +134°$ (c=0.20; MeOH).

To a suspension of 6.1 g (0.015 mol) of this salt in 200 ml of ethyl acetate there are added 20 ml of ammonia, the mixture is stirred for 5 mn at 20° C., decanted, the aqueouse phase is extracted with ethyl acetate, the organic phase is washed with water and dried over magnesium sulphate. 3.8 g of free base are obtained. $[\alpha]_D^{20} = +9.7°$ (c=0.32; MeOH).

To a solution of 3.5 g (0.014 mol) of this base in 50 ml of isopropyl alcohol, there are added 140 ml of a 0.1N solution of hydrochloric acid in isopropyl alcohol. The solution is stirred for 5 mn at 20° C., then the alcohol is evaporated under vacuum, the salt is washed with ethyl acetate and dried.

Melting point: 249°–251° C. $[\alpha]_D^{20} = +173°$ (c=0,224; EtOH).

(f) Laevo-rotatory enantiomer.

The residue (21 g) from the evaporation of the mother liquors from the crystallization of the dextro-rotatory isomer tartrate is suspended in 300 ml of ethyl acetate, and then treated with ammonia. The mixture is stirred for 5 mn, then decanted, the aqueous phase is extracted with ethyl acetate, the organic phase is washed with water and dried over magnesium sulphate. 13 g of free base are obtained.

7.25 g (0.028 mole) of this base in solution in 200 ml of methanol are treated with a solution of 4.3 g (0.028 mol) of (−)-tartaric acid in 100 ml of methanol. After stirring for 5 mn at 20° C. the solvent is evaporated under vacuum and the residue is recrystallized in methanol. Melting point: 227°–230° C. $[\alpha]_D^{20} = -133°$ (c=0.23; MeOH). To a suspension of 6.2 g of this salt in 200 ml of ethyl acetate there are added 20 ml of ammonia, the mixture is stirred for 5 mn at 20° C., then decanted, the aqueous phase is extracted with ethyl acetate, the organic phase is washed with water, dried over magnesium sulphate and evaporated. 3.65 g of free base are obtained. $[\alpha]_D^{20} = -9.5°$ (c=0.22; MeOH). To a solution of 3.5 g (0.014 mol) of this base in solution in 50 ml of isopropyl alcohol there are added 140 ml of a 0.1N solution of hydrochloric acid in isopropyl alcohol. The mixture is stirred for 15 mn at 20° C., the alcohol is evaporated under vacuum and the residue is washed with ethyl acetate.

Melting point: 249°–251° C. $[\alpha]_D^{20} = -168.1°$ (c=0.22; EtOH).

EXAMPLE 2

2-(4,5-Dihydro-1H-imidazol-2-yl)-8-fluoro-1,2,4,5-tetrahydropyrrolo[3,2,1-hi]indole (a) N,N-dimethyl-2-(4-fluoro-2-nitrophenyl)etheneamine.

In a 1,000-ml flask equipped with a magnetic stirrer, condenser and placed under argon, there are introduced 60.6 g (0.39 mol) of 4-fluoro-2-nitrotoluene, 143 g (1.2 mol) of N,N-dimethyl (dimethoxymethyl) amine and 400 ml of dimethylformamide.

The mixture is refluxed for 6 h, and then further 47.7 g of N,N-dimethyl (dimethoxymethyl)amine in solution in 150 ml of dimethylformamide are added.

After stirring for 8 hours at reflux temperature the mixture is left to cool, and then poured into iced water. The aqueous phase is extracted with diethyl ether, the organic phase is washed with water, then dried over sodium sulphate, and the solvent is evaporated. There remain 82.8 g of a reddish oil which is used, as it is, in the following stage.

(b) 6-Fluoro-1H-indole.

In a 1.7 l stainless steel Parr flask there are introduced 41.4 g (0.197 mol) of the oil of Example 2a), 500 ml of ethanol and 5 g of wet Raney nickel, and a hydrogenation is performed at about 0.44 MPa maximal pressure for 30 mn. Then the catalyst is filtered off, rinsed with ethnaol, and the filtrate is evaporated under vacuum. The residue is purified by chromotagraphy on a silica column with dichloromethane as eluent.

39.4 g of pure 6-fluoro-1H-indole are obtained. Melting point: 68°–70° C.

(c) 6-Fluoro-2,3-dihydro-1H-indole.

91 g (1.45 mole) of sodium cyanoborohydride are added portionwise to a solution of 55.8 g (0.41 mole) of 6-fluoro-1H-indole in 1.2 l of acetic acid, while maintaining the temperature of the reaction mixture between 10° and 15° C. The mixture is stirred for 2.5 hours, then poured into 6 kg of ice, and sodium hydroxide is added until the pH is greater than 10.

The mixture is stirred for 30 mn and then extracted with 3 l of diethyl ether. The organic phase is washed with water, dried over sodium sulphate and evaporated under vacuum. There remain 54.6 g of a residue which is used, as it is, in the following stage.

(d) 6-Fluoro-2,3-dihydro-1-nitroso-1H-indole.

In a 1,000-ml three necked flask equipped with a magnetic stirrer and dropping funnel there are introduced the 54.6 g (0.4 mole) of the product of Example 2c), and 400 ml of 25 % strength aqueous sulphuric acid. The mixture is cooled and, while maintaining the temperature between −10° and −5° C., a solution of 31.1 g (0.45 mol) of sodium nitrite in 60 ml of water is added dropwise. The solution becomes viscous; it is stirred at −5° C. for another 30 mn, and then extracted with dichloromethane. The organic phase is washed with water until it is neutral, it is dried over sodium sulphate and evaporated under vacuum. There remain 66.4 g of a product which is used, as it is, in the following stage.

(e) 6-Fluoro-2,3-dihydro-1H-indole-1-amine.

In a 6-l three-necked flask equipped with a magnetic stirrer, condenser, thermometer and dropping funnel, and placed under argon, there are introduced 16.3 g (0.43 mol) of aluminum and lithium hydride and 500 ml of tetrahydrofuran. The suspension is heated to about 50° C. and then a solution of 64.6 g (0.39 mol) of 6-fluoro-2,3-dihydro-1-nitroso-1H-indole in 500 ml of tetrahydrofuran is added dropwise. Then the mixture is stirred for 4 hours, and hydrolyzed by successive additions of 14 ml of water, 14 ml of .1N sodium hydroxide and 42 ml of water.

The mixture is still stirred for 30 mn, the inorganic solid is separated by filtration and rinsed with diethyl ether, the filtrate is dried over sodium sulphate and the solvents are driven off under vacuum.

37.6 g of an oil is obtained, which is used, as it is, in the following stage.

(f) Ethyl 2-(6-fluoro-2,3-dihydro-1H-indol-1-yl)imino-propanoate.

In a 1,000-ml flask equipped with a magnetic stirrer and condenser, and placed under argon, there are introduced 37.6 g (0.25 mol) of the indolamine of Example 2e), 300 ml of ethanol, 32.5 g (0.28 mol) of ethyl 2-oxopropanoate and 2 ml of acetic acid, and the mixture is stirred at reflux temperature for 2 hours.

After cooling, the solvents are driven off under vacuum and the residue is purified by chromatography through a silica column with dichloromethane as eluent. 46.6 g of purified compound are obtained.

(g) Ethyl 8-fluoro-4,5-dihydro-pyrrolo[3,2,1-hi]indole-2-carboxylate.

In a 250-ml Keller flask equipped with a magnetic stirrer and placed under argon, there are introduced 37.1 g (0.15 mol) of the compound of Example 2f, and 105 ml of acetic acid. The mixture is heated to 80° C. and, in the course of 10 mn, 26 ml (30 g or 0.21 mol) of boron trifluoride etherate are added dropwise.

The temperature is raised to 90° C. and the stirring is maintained for 1 h.

The mixture is poured into 400 ml of water, the aqueous phase is extracted with diethyl ether, the ether phase is washed with a saturated aqueous solution of sodium bicarbonate, then with water, and then dried over sodium sulphate. The solvents are evaporated and the residue is purified by chromatography through a silica column with dichloromethane as eluent. 8.4 g of pure compound are obtained.

Melting point: 98°–100° C.

(h) Ethyl 8-fluoro-1,2,4,5-tetrahydro-pyrrolo[3,2,1-hi]indole-2-carboxylate.

In a 1,000-ml three-necked flask equipped with a magnetic stirrer, condenser and thermometer, there are introduced 170 ml of ethanol which is saturated by bubbling in gaseous hydrochloric acid.

14 g (0.06 mol) of the compound of Example 2 g) are added, further hydrochloric acid is bubbled in at −40° C., and then 30 g (0.25 gram-atom) of granular tin are added.

The mixture is stirred at 20° C. for 24 h, the solvent is evaporated under vacuum, 500 ml of absolute ethanol are added, the mixture is cooled to −10° C. and ammonia is bubbled in until the pH value is greater than 9.

The alcohol is evaporated under vacuum, the residue is taken up with 500 ml of diethyl ether, the solid is filtered off and rinsed with diethyl ether and the filtrate is evaporated under vacuum.

13.6 g of a compound is obtained, which is used, as it is, in the following stage.

(i) 2-(4,5-dihydro-1H-imidazol-2-yl)-8-fluoro-1,2,4,5-tetrahydro-pyrrolo[3,2,1-hi]indole.

In a 250-ml Keller flask equipped with a magnetic stirrer, thermometer, Dean-Stark apparatus, and placed under argon, there are introduced 90 ml of toluene and 58.4 ml (10.1 g or 0.14 mol) of trimethylaluminum at 25.2% strength in hexane. The mixture is cooled to −10° C. and, in the course of 15 mn, a solution of 9,4 ml (8.4 g or 0.14 mol) of ethylenediamine in 30 ml of toluene is added.

The temperature is left to raise to 0° C. in 10 mn, then the mixture is heated to 50° C. and, at this temperature, 13.3 g (0.0565 mol) of the compound of Example 2h) are added, in solution in 90 ml of toluene.

The mixture is stirred at 110° C. for 3 hours, the hexane being eliminated with the Dean-Stark apparatus, then it is cooled to −10° C. and hydrolyzed with 59 ml of water.

200 ml of ethyl acetate are added, the solid is filtered off and rinsed with ethyl acetate, the organic phase is washed with a saturated sodium chloride solution, dried over sodium sulphate, and the solvent is driven off under vacuum.

13.4 g of crude compound are obtained. The hydrochloride salt is prepared by introducing 13.4 g (0.0565 mol) of this compound and 565 ml of 0.1M hydrochloric isopropyl alcohol into a 1,000-ml flask equipped with a stirrer. The solution is stirred for 15 mn, the solvent is evaporated under vacuum, and the residue is recrystallized from 80 ml of ethanol, filtered and dried at 90° C. under vacuum. 7.3 g of crystals are obtained.

Melting point: 261°–263° C.

(j) Dextro-rotatory enantiomer.

8 g (0.035 mol) of the crude racemate (base) of Example 2i), in solution in 250 ml of methanol, are treated with 13.02 g (0.035 mol) of (+)-dibenzoyltartaric acid.

The mixture is stirred for 1 hour at 20° C., the solvent is evaporated under vacuum and the residue is recrystallized three times from methanol, the mother liquors being preserved each time. 6 g of dibenzoyltartrate are so obtained. Melting point: 190°–195° C. $[\alpha]_D^{22} = +171°$ (c=0.2; MeOH). 200 ml of ethyl acetate and 20 ml of ammonia are added to this salt, the mixture is stirred for 5 mn, the organic phase is separated, and the aqueous phase is extracted once more with ethyl acetate.

Both organic phases are combined, washed with water, dried over magnesium sulphate, and evaporated. 2 g of dextrorotatory enantiomer are obtained, in form of the free base. Melting point: 120°–125° C. $[\alpha]_D^{22} = +173,5°$ (c=0.275; MeOH).

The hydrochloride is prepared by dissolving 1.8 g of this base in 20 ml of isopropyl alcohol and adding 85 ml of 0.1N hydrochloric isopropyl alcohol. The mixture is stirred for 5 mn at 20° C., the solvent is evaporated under vacuum and the residue is washed with ethyl acetate.

Melting point: 262°–265° C. $[\alpha]_D^{22} = +225°$ (c=0.275; EtOH).

(k) Laevo-rotator enantiomer.

The mother liquors from the recrystallizations of Example (2j) are combined, then evaporated, and the 12 g of residue are suspended in 300 ml of ethyl acetate. 20 ml of ammonia are added, the mixture is stirred for 5 mn, the organic phase is separated, and the aqueous phase is extracted once more with ethyl acetate.

Both organic phases are combined, washed with water, dried over magnesium sulphate and evaporated. 4.7 g of free base are obtained, with a high content of laevorotatory enantiomer. This base is dissolved in 200 ml of methanol and a solution of 7.5 g of (−)-dibenzoyltartaric acid in 50 ml of methanol is added. The mixture is stirred for 5 mn at 20° C., the solvent is evaporated under vacuum and the residue is recrystallized twice in methanol. 5.5 g of salt are obtained. Melting point: 187°–190° C. $[\alpha]_D^{22} = -179,6°$ (c=0.3; MeOH).

This salt is suspended in 200 ml of ethyl acetate, 20 ml of ammonia are added, the mixture is stirred for 5 mn, the organic phase is separated, and the aqueous phase is extracted once more with ethyl acetate.

Both organic phases are combined, washed with water, dried over magnesium sulphate and evaporated. 1.5 g of laevo-rotatory enantiomer are obtained, in form of the free base. Melting point: 123°–125° C. $[\alpha]_D^{22} = -171°$ (c=0.23; MeOH).

The hydrochloride is prepared by dissolving 1.7 g of this base in 30 ml of isopropyl alcohol and adding 80 ml of 0.1N hydrochloric isopropyl alcohol. The mixture is stirred for 5 mn at 20° C., the solvent is evaporated under vacuum, and the residue is washed with ethyl acetate.

Melting point: 258°–261° C. $[\alpha]_D^{22} = -222,6°$ (c=0.2; EtOH).

The table which follows illustrates compounds prepared according to the invention.

TABLE

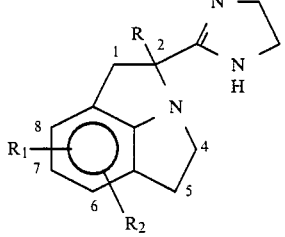

(I)

| No | $R_1$ | $R_2$ | R | Salt | m.p. (°C.) |
|---|---|---|---|---|---|
| 1 | H | H | $nC_3H_7$ | hydrochloride | 255 (decomp.) |
| | dextrorotatory isomer | | | hydrochloride | 249–251 |
| | | | | $[\alpha]_D^{20} = +173°$ | (c = 0,224; EtOH) |
| | laevorotatory isomer | | | hydrochloride | 249–251 |
| | | | | $[\alpha]_D^{20} = -168,1°$ | (c = 0,22; EtOH) |
| 2 | H | H | H | fumarate | 184–186 |
| 3 | H | H | $CH_3$ | fumarate | 192–194 |
| 4 | H | H | $C_2H_5$ | fumarate | 162–164 |
| 5 | H | H | $nC_4H_9$ | fumarate | 171–173 |
| 6 | 8-Cl | H | H | fumarate | 195–196 |
| | | | | hydrochloride | 268–270 |
| 7 | 8-Cl | H | $CH_3$ | fumarate | 94–99 |
| 8 | 8-Cl | H | $nC_3H_7$ | fumarate | 202–204 |
| 9 | 7-F | H | H | fumarate | 137–141 |
| 10 | 7-F | H | $CH_3$ | fumarate | 147–150 |
| 11 | 7-F | H | $nC_3H_7$ | fumarate | 200–203 |
| 12 | 7-$CH_3$ | H | H | fumarate | 168–172 |
| 13 | 7-$CH_3$ | H | $nC_3H_7$ | fumarate | 178–180 |
| 14 | 6-$CH_3$ | 8-$CH_3$ | H | fumarate | 217–219 |
| 15 | 6-$CH_3$ | 8-$CH_3$ | $CH_3$ | fumarate | 207–210 |
| 16 | 6-$CH_3$ | 8-$CH_3$ | $nC_3H_7$ | fumarate | 180–185 |
| 17 | 8-Cl | H | $C_2H_5$ | fumarate | 171–173 |
| | | | | hydrochloride | 285–287 |
| 18 | 8-F | H | H | fumarate | 174–176 |
| | | | | hydrochloride | 261–263 |
| | dextrorotatory isomer | | | hydrochloride | 262–265 |
| | | | | $[\alpha]_D^{22} = +225°$ | (c = 0,275; EtOH) |
| | laevorotatory isomer | | | hydrochloride | 258–261 |
| | | | | $[\alpha]_D^{20} = -222,6°$ | (c = 0,2; EtOH) |
| 19 | 8-F | H | $CH_3$ | hydrochloride | 256–258 |
| 20 | 8-F | H | $nC_3H_7$ | fumarate | 186–188 |
| 21 | 6-Cl | H | H | fumarate | 165–170 |
| | | | | hydrochloride | 274–277 |
| 22 | 6-Cl | H | $CH_3$ | hydrochloride | 275–277 |
| 23 | 6-Cl | H | $nC_3H_7$ | hydrochloride | 246–248 |
| 24 | 6-$CH_3$ | H | H | fumarate | 217–222 |
| 25 | 6-$CH_3$ | H | $nC_3H_7$ | fumarate | 171–175 |
| 26 | H | H | $iC_4H_9$ | fumarate | 180–183 |

The compounds useful according to the invention were subjected to pharmacological tests with respect to the decrease in the hyperglycaemia induced by oral glucose administration to mice.

Male CD mice weighing 25–30 g were used. They had free access to food throughout the study. They were administered intraperitoneally with saline solution or compounds of the invention (10 mg/kg) and treated with glucose (1 g/kg p.o.) 20 minutes later. 30 minutes following this treatment they were quickly decapitated and their trunk blood (0.5–1 ml) was collected in Eppendorf tubes containing heparine (50 u.i.), sodium fluoride and EDTA mixture (Boehringer-Mannheim). The blood was immediately centrifuged for 2 minutes and plasma (200–700 μl) was collected and assayed for glucose. With comparison to the control animals, treated with saline solution, the experiment animals, treated with the compounds of the invention, especially with compounds 1 and 18 of the Table (racemates or dextro-rotatory enantiomers) showed a substantial decrease in the hyperglycaemia, an effect most likely due to an increase in the release of insulin from the pancreas.

The results of the tests demonstrate that the compounds of the invention are useful as antiabetics, especially for the treatment of non-insulin-dependent diabetes (type II). Therefore they can be used for the preparation of antidiabetic pharmaceutical compositions suitable for oral or parenteral administration, for example in the form of capsules, tablets, pellets, gelatine capsules, or syrups, suspensions or solutions to be taken orally or parenterally, optionally combined with suitable excipients.

The pharmaceutical compositions can contain also other active substances such as known antidiabetics, or substances strengthening their effects, or substances preventing or reducing the complications related with diabetes.

The daily dosage can range from 5 to 100 mg per os.

We claim:

1. A method of treating diabetes in a patient, which comprises administering to said patient an effective antidiabetic amount of a compound of the general formula (I)

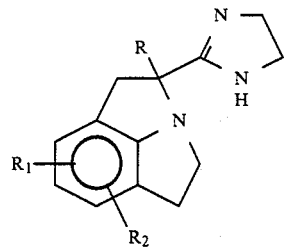

in which R is hydrogen or a linear or branched $C_{1-4}$ alkyl group, and $R_1$ and $R_2$, which may be the same or different, are hydrogen, halogen or $C_{1-4}$ alkyl, said compound being in the form of a pure enantiomer or of a mixture of enantiomers, or an addition salt thereof with a pharmaceutically acceptable acid.

2. A method according to claim 1, wherein said compound is 2-(4,5-dihydro-1H-imidazol-2-yl)-2-propyl-1,2,4,5-tetrahydropyrrolo[3,2,1-hi]indole.

3. A method according to claim 1, wherein said compound is the dextro-rotatory enantiomer of 2-(4,5-dihydro-1H-imidazol-2-yl)-2-propyl-1,2,4,5-tetrahydro-pyrrolo[3,2,1-hi]indole.

4. A method according to claim 1, wherein said compound is 2-(4,5-dihydro-1H-imidazol-2-yl)-8-fluoro-1,2,4,5-tetrahydropyrrolo[3,2,1-hi]indole.

5. A method according to claim 1, wherein said compound is the dextro-rotatory enantiomer of 2-(4,5-dihydro-1H-imidazol-2-yl)-8-fluoro-1,2,4,5-tetrahydro-pyrrolo[3,2,1-hi]indole.

* * * * *